(12) United States Patent
Ricchiuto et al.

(10) Patent No.: US 9,072,754 B2
(45) Date of Patent: Jul. 7, 2015

(54) PROCESS FOR OBTAINING NON-ALLERGIC PROPOLIS

(75) Inventors: Giuseppe Maria Ricchiuto, Verona (IT); Claudio Sebastiano Gardana, Bergamo (IT); Simone Domenico Guglielmetti, Milan (IT)

(73) Assignee: MR. GIUSEPPE MARIA RICCHIUTO (IT)

( * ) Notice: Subject to any disclaimer, the term of this patent is extended or adjusted under 35 U.S.C. 154(b) by 148 days.

(21) Appl. No.: 13/634,666

(22) PCT Filed: Mar. 15, 2011

(86) PCT No.: PCT/IB2011/051086
§ 371 (c)(1),
(2), (4) Date: Sep. 13, 2012

(87) PCT Pub. No.: WO2011/114291
PCT Pub. Date: Sep. 22, 2011

(65) Prior Publication Data
US 2013/0006011 A1   Jan. 3, 2013

(30) Foreign Application Priority Data
Mar. 16, 2010   (IT) .............................. VR2010A0050

(51) Int. Cl.
*A61K 35/644*   (2015.01)

(52) U.S. Cl.
CPC .................................... *A61K 35/644* (2013.01)

(58) Field of Classification Search
CPC ..... C07C 69/732; C07C 67/52; A61K 35/644
USPC .................................. 562/531, 559; 422/187
See application file for complete search history.

(56) References Cited

FOREIGN PATENT DOCUMENTS

| CN | 1 162 613 | 10/1997 |
|---|---|---|
| EP | 0 109 993 A1 | 6/1984 |
| EP | 0 529 962 A2 | 3/1993 |
| EP | 1 985 191 | 10/2008 |
| JP | 7-8185 | 1/1995 |
| JP | 2007-053947 | 3/2007 |
| WO | WO 2009/111848 A1 | 9/2009 |
| WO | WO 2009/133073 A1 | 11/2009 |

OTHER PUBLICATIONS

Burdock, Food and Chemical Toxicology 36 (1998), p. 347-363 (IDS).*
Guglielmetti et al. Applied and Enviromental Microbiology, (2008), 74(4), p. 1284-1288 (IDS).*
Giusti et al. Contact Dermatitis, (2004), vol. 51, p. 255-258 (disclosed by applicants).*
International Search Report and Written Opinion dated Aug. 22, 2011 issued in corresponding international patent application No. PCT/IB2011/051086.
Chinese Office Action mailed Aug. 14, 2014 in corresponding Chinese Application No. 201180014028.5, along with an English language translation of portions thereof.
Duo-gang Zhou et al., "Determination of total flavone in manufacture of beesglue," Journal of Anhui Institute of Mechanical Electrical Engineering, vol. 15, No. 1, pp. 67-71, Mar. 2000, (English language abstract on p. 71).
Simone Guglielmetti et al., "Bacterial Cinnamoyl Esterase Activity Screening for the Production of a Novel Functional Food Product," Applied and Environmental Microbiology, vol. 74, No. 4, pp. 1284-1288, Feb. 2008.
G.A. Burdock, "Review of the Biological Properties and Toxicity of Bee Propolis (Propolis)," Food and Chemical Toxicology, vol. 36, pp. 347-363, Jan. 1998.
Hideki Miyataka et al., "Evaluation of Propolis. I. Evaluation of Brazilian and Chinese Propolis by Enzymatic and Physico-Chemical Methods," Biological & Pharmaceutical Bulletin, vol. 20, No. 5, pp. 496-501, Jan. 1997.
Hideki Miyataka et al., "Evaluation of Propolis (II): Effects of Brazilian and Chinese Propolis on Histamine Release from Rat Peritoneal Mast Cells Induced by Compound 48/80 and Concanavalin A," Biological & Pharmaceutical Bulletin, vol. 21, No. 7, pp. 723-729, Jul. 1998.
L.G. Coelho et al., "Brazilian green propolis on *Helicobacter pylori* infection, a pilot clinical study," *Helicobacter*, 12(5):572-574, Oct. 2007 (Abstract only).

* cited by examiner

*Primary Examiner* — Yong Chu
(74) *Attorney, Agent, or Firm* — Ostrolenk Faber LLP (57) ABSTRACT

The present disclosure relates to a process for pre-treating raw *propolis* comprising at least one allergenic activity substance, which comprises reacting *propolis* with a probiotic microorganism containing one or more cinnamoyl-esterase activity enzymes to obtain a semisolid *propolis* derivative substantially without or impoverished of allergenic substances. The present invention also relates to a method of purifying semisolid *propolis* derivative to obtain a hydroalcoholic hydrodispersible *propolis* derivative.

13 Claims, 3 Drawing Sheets

Fig. 1. Effect of incubation temperature on degradation of caffeic acid esters

Fig. 2. Effect of incubation time on degradation of caffeic acid esters.

Fig. 3. Effect of ethanol percentage on cinnamoyl esterase activity.

Fig. 4. Degradation of 3-methyl-2-butenyl caffeate depending on bacterial cells number.

Fig. 5. Histogram 1. Degradation of allergenic esters after treatment of raw propolis for 24h with LH5.

PROCESS FOR OBTAINING NON-ALLERGIC PROPOLIS

The present invention relates to a process for obtaining a derivative of *propolis* having a reduced content in allergenic substances thereby making its use substantially without contraindications to human health, a method of treating raw *propolis* or a derivative thereof, and a hydroalcoholic derivative of *propolis* for being used advantageously in the nutraceutic and cosmetic field.

*Propolis* produced by bees (*Apis mellifera*) is obtained from resinous exudates of the plants bark and leaf buds, e. g. poplar, beech, birch, chestnut, pine, etc, which are collected and processed by bees through their salivary secretions and wax addition.

At room temperature, *propolis* appears as a sticky and malleable substance, having an aromatic smell and a different colour depending on the source plant. Its chemical composition depends on the original plant of the resinous exudate, as well as the provenance area and the collection season. *Propolis* coming from plants of the *Populus* genus consists of resin (20-55%), wax (30-40%), volatile oils (5-10%), and various phenol compounds (10-30%), including, in particular, flavonoids. The phenolic portion also comprises phenylalkyl acids, such as cinnamic acid, caffeic acid, ferulic acid and p-coumaric acid and some esters thereof.

Owing to some components thereof, *propolis* has numerous biological and pharmacological properties, including antibacterial, antiviral, antifungal, anti-inflammatory, antioxidant, immunostimulating, cariostatic, anti-tumour and anti-*Helicobacter pylori* activity (L. G. Coelho et al., "*Brazilian green propolis on Helicobacter pylori infection. A pilot clinical study*", *Helicobacter* Vol. 12: 572-4 (2007)).

For these properties, the use of *propolis*-based preparations has been known for a long time in popular medicine and the main applications relate to treatment of respiratory tract infections, flu, acne, wounds, burns, herpes, gingivitis and stomatitis, as well as prevention of caries. *Propolis* is also used in the cosmetics field for the formulation of creams, ointments, shampoos, lotions, gels and the like.

However, besides many beneficial effects, the use of *propolis* can cause some undesired effects, such as mouth dryness, slight gastric disorders and allergic skin reactions (allergic contact dermatitis) in particularly sensitive people (*Contact dermatitis*, Vol. 17: 163 (1987); *Pediatr. Dermatol.* Vol. 22: 1 (2005); *Contact dermatitis*, Vol. 51: 255 (2004)).

Recent studies (F. Giusti, "*Sensitization to propolis in 1255 children undergoing patch testing*"; *Contact Dermatitis*, Vol. 51: 255-258 (2004)) have shown that such allergic reactions are attributable to a well-defined mixture of *propolis* components, termed LB-1, consisting of caffeic acid and some esters thereof of general formula (1)

(1)

wherein R can be: 3-methyl-2-butenyl, 2-methyl-2-butenyl, 3-methyl-3-butenyl, benzyl and phenylethyl.

These compounds are present in the LB-1 fraction in different percentages, e.g. 3-methyl-2-butenyl caffeate (54%), 3-methyl-3-butenyl caffeate (28%), 2-methyl-2-butenyl caffeate (4%), phenylethyl caffeate (8%), benzyl caffeate (1%) and caffeic acid (1%) (DeGroot A. C., Weyland J. W, Nater J. P., *Unwanted effects of cosmetics and drugs used in dermatology*, pp. 770, Elsevier, N.Y., 1994). Among these compounds, 3-methyl-2-butenyl-caffeate shows the most allergenic effect, as reported in *Food Chem. Toxicology*, Vol. 36: 34763 (1998).

*Propolis* also comprises 3-methoxy-caffeic acid (or ferulic acid) and 3,4-dimethoxy-caffeic acid esters, although they are not considered to have allergenic activity (*Contact Dermatitis*, Vol. 23: 274-75, (1990)).

To eliminate allergic reactions of *propolis*, several methods have been suggested, such as that described in patent document WO 2009/133073, in which a chemical or physical-chemical process is disclosed for obtaining an effective hypoallergenic *propolis* extract. This process comprises a series of steps including *propolis* extraction by a solvent, such as an alcohol and water mixture, which is performed at a temperature higher than 25° C., a first separation of insoluble material at a reaction temperature equal to room temperature, a second separation of insoluble substances at a temperature lower than 0° C., and removal of the extraction medium. However, this method has some drawbacks. First of all, the working times are generally long, especially because a decrease in temperature provided by the process must gradually occur in order to allow for the formation and quantitative precipitation of practically insoluble substances, thus requiring a careful and accurate monitoring. Thus, equipment and/or plants ensuring high accuracy in temperature control are required.

Another disadvantage is that removal of insoluble material by precipitation and filtration never takes place completely, since, as known, every compound has a specific solubility in a solvent, even if very low. Thus, in order to get the best results, it is necessary to repeat the precipitation and filtration steps. It is clear then that manufacturing costs are obviously high.

Moreover, the above described method, by not being selective, cannot ensure that the biological/pharmacological efficacy of the obtained extract is maintained. Furthermore, the method disclosed in WO 2009/133073 does not show the effective reduction of the allergenic substances content in *propolis*.

Another method for eliminating the allergenic reactions of *propolis* is disclosed in the Japanese patent application no. JP-7-8185, which teaches an enzymatic method for eliminating some allergenic substances from *propolis*, without affecting the pharmacologic properties thereof and causing allergenicity. In this prior art document, the substances said to be allergenic are some esters of caffeic acid, more particularly isoprenyl caffeate acid and phenylethyl caffeate, that are enzymatically removed by means of hydrolase or oxidoreductase. The hydrolase is preferably an esterase and more preferably a carboxylesterase, whereas the oxidoreductase is preferably laccase, tyrosinase, phenolase, bilirubin oxidase or peroxidase.

According to JP-7-8185, the enzymes are selected for their high specificity, and should the enzymes be accurately selected, degradation from *propolis* of the undesired compounds is obtained. In order to illustrate such a theory according to JP-7-8185, standards and *propolis* have been incubated together with the enzymes, and after the extraction the residual amount of isoprenyl caffeate and phenylethyl caffeate has been evaluated by means of LC-UV or GC-FID.

The limits of the method taught by JP-7 8185 are both conceptual and methodological. As a matter of fact, laccase, tyrosinase, phenolase, bilirubin oxidase or peroxidases are non specific oxide-reductive-activity enzymes. Such enzymes actually have a substrate including the phenolic or catecholic residue, which changes to quinone or diquinone, respectively, leading to a successive polymerization of products.

JP-7 8185 teaches that a gel permeation (LC-GPC-UV) is carried out in order to detect the coming up of polymers after the enzymatic reaction.

However, each flavonoid (the active fraction of *propolis*) includes the phenolic or catecholic residue. Thus, flavonoids also become highly degraded by oxidoreductase. Hereinafter, the structure of a flavonoid is shown, in which phenolic or catecholic residues can be attacked by the oxide-reductive activity enzymes.

According to JP-7 8185, the content of flavonoids before and after the enzymatic reactions is not evaluated, and therefore it is not possible to know how their content is changed. Moreover, the dosage of allergenic substances, i. e. isoprenyl caffeate and phenylethyl caffeate, has been carried out in a poorly specific way, more particularly in so far as the analysis of the *propolis* samples is concerned. Evaluations have been carried out by means of gas-chromatography with a hydrogen flame ionization detector (FID), which can identify the compounds solely by comparing their retention time. The determinations carried out by means of liquid chromatography (HPLC-UV) are scarcely reliable, bearing in mind the complex structure of *propolis* and that the allergenic substances are a minor part of *propolis*, and thus for correctly identifying and quantifying them, a sensible and accurate method must be used to also prevent the elimination of an active part of *propolis* (such as flavonoids).

Also the procedure used in JP-7 8185 in order to cause a reaction of the substrates with the enzyme is questionable. First of all, *propolis* is dispersed in ethanol for a week, and subsequently the alcoholic degree has been decreased with water down to 10%. A small fraction of liquid, i.e. 10 ml, has been reacted with the enzyme (100 mg), and 8 hours later the mixture has been distilled and analyzed by means of gas-chromatography. According to such prior art document, the alcoholic degree must be reduced to cause the enzyme to act. Should the solution be entirely ethanolic, the enzyme could be denatured causing a substantial loss of activity thereof.

Moreover, the enzymes used in JP-7-8185 are expensive since they are industrially obtained.

Accordingly, clearly such a procedure cannot be industrialized, as the ethanol and the enzymes are quite expensive.

Furthermore, according to JP-7-8185 an amount ranging from 0.1 to 0.5 g of enzyme per gram of *propolis* is used or from 10 to 50 g of enzyme if the incubation time ranges from 1 to 3 days. Thus, the method taught by JP-7-8185 besides being expensive is also time consuming and incompatible with the needs of industry.

EP-0 109 993 teaches the preparation of purified extracts of *propolis* by extraction with an organic solvent for a time interval ranging from 1 to 10 days, cooling and filtration of the suspension thus obtained. The filtrate is then used for preparing different formulations. Owing to such a procedure the obtained extract is not hydrodispersible since the high amount of solvent keeps in solution the fat portion, including a wax portion present in the *propolis*. The time required for the extraction ranges from 1 to 10 days, and this fact together with absence of control of the temperature render such a method poorly applicable on an industrial scale. Thus, the extract obtained is not standardized or standardizable.

EP-0 109 993 also teaches extraction of the raw *propolis* with aqueous ethanol solutions at a concentration of ethanol ranging from 10 to 25% volume/volume to obtain hydrosoluble extracts.

CN-1 162 613 and WO-2009/133 073 disclose an hydroalcoholic extract of *propolis* obtained by the following sequence: extraction of raw *propolis* with ethanol to obtain a suspension, filtration in order to remove the residual solid, cooling the solution to a temperature of 0° C. or less, and filtration of the suspension to eliminate insoluble materials and obtain a purified extract.

The extracts thus obtained are not standardized neither in the content of active principles nor in the amount of fats. At the end of the extraction process, if the solvent (ethanol) is evaporated, i.e, removed from the extract and, new ethanol is subsequently added to obtain a titred extract, there would be an exorbitant waste of expensive materials. Clearly, such a process cannot be carried out on an industrial scale, as ethanol is a very expensive industrial product and during the process would be caused to evaporate and thus it would be wasted.

According to the methods described in the above-mentioned prior art documents, it is not possible to a priori establish and thus standardize the content of active principles in *propolis*. Moreover, allergenic substances are said to be removed, but no analysis is reported as to the actual evaluation of the content thereof, and thus such a removal is undemonstrated.

The main object of the present invention is to provide a process for eliminating or substantially reducing the allergenic components contained in solid raw *propolis*.

Another object of the present invention is to provide a method of treatment and purification of *propolis* that maintains its organoleptic features and content in active principles typical of raw *propolis*.

Another object of the present invention is to provide *propolis* extracts which can be dispersed in water; i.e. having an extremely reduced amount of fat substances, such as waxes, therein.

A further object of the present invention is that such process and method are completely safe for both production staff and the end-user of raw *propolis*.

Another object of the present invention is to provide a cost-effective feasible method for treating and purifying *propolis*.

Another object of the present invention is to provide a pre-treated *propolis* derivative as obtained by the process of the present invention.

A further object of the present invention is to provide a *propolis* hydro-alcoholic derivative as obtained by the purification method of the present invention.

A not least object of the present invention is to provide a hydroalcoholic derivative of *propolis* for use in the nutraceutics and cosmetics field with no contraindications due to allergenic activity.

According to a first aspect of the present invention there is provided a process for pre-treating *propolis* comprising at least one allergenic substance of general formula (1), wherein R is an alkyl or alkenyl selected from the group comprising 3-methyl-2-butenyl, 2-methyl-2-butenyl, 3-methyl-3-butenyl, benzyl and phenylethyl, characterized in that *propolis* is caused to react with probiotic microorganisms containing at least one enzyme having selective cinnamoyl-esterase activity to obtain a semisolid *propolis* derivative substantially lacking or impoverished of allergenic substances.

According to a further aspect of the present invention there is provided a semisolid derivate of *propolis* obtained by the process according to the present invention, having a reduced content of one or more allergenic substance compared to raw *propolis*, said content being lower than 0.5%, such a reduction being higher than 60%.

The process according to the present invention for pre-treating raw *propolis* is aimed at reducing its content in allergenic compounds of the above-reported general structure formula (1).

The process substantially comprises a working step including putting in contact and reacting raw *propolis* or a *propolis*-based preparation with a specific microorganism comprising one or more enzymes having selective cinnamoyl-esterase activity to obtain a derivate in semisolid state.

Advantageously, the enzyme(s) having selective esterase activity comprise(s) at least one cinnamoyl esterase.

Enzymes having esterase activity, in particular the cinnamoyl esterase, are obtained from bacteria of *Lactobacillus, Carnobacterium, Enterococcus, Streptococcus* and *Bifidobacterium* genus, some of which are listed in Table 1 hereinafter, where also a source thereof is indicated.

TABLE 1

| Microorganisms where enzymes having esterase activity are present | | |
|---|---|---|
| Type | Species | Source |
| Lactobacillus | L. paracasei | Human intestine |
| | L. paracasei | Fermented milk |
| | L. paracasei | International culture collection |
| | L. acidophilus | Fermented milk |
| | L. acidophilus | International culture collection |
| | L. helveticus | Dairy starters |
| | L. casei | Human intestine |

TABLE 1-continued

| Microorganisms where enzymes having esterase activity are present | | |
|---|---|---|
| Type | Species | Source |
| | L. fermentum | Human intestine |
| | L. rhamnosus | Human intestine; commercial probiotics |
| Carnobacterium | C. Carnobacterium | Meat |
| | C. maltaromaticum | Fish |
| | C. maltaromaticum | Milk |
| | C. divergens | Meat |
| Enterococcus | E. faecalis | Cheese |
| | E. faecium | Cheese |
| Streptococcus | S. thermophilus | Yogurt |
| Bifidobacterium | B. bifidum | Human faeces |
| | B. pseudocatenulatum | Faeces |
| | B. longum | Human faeces |
| | B. animalis sottosp. lactis | Commercial probiotic product |
| | B. adolescentis | Human faeces |

Preferably, cinnamoyl esterase enzyme is produced by a number of bacterial species of *Lactobacillus* and *Enterococcus* genus and specifically by bacterial strain of *Lactobacillus helveticus, Lactobacillus acidophilus, Lactobacillus fermentum, Lactobacillus casei, Lactobacillus rhamnosus, Enterococcus faecalis* species and the like. Preferably, cinnamoyl esterase enzyme is produced by a *Lactobacillus helveticus* strain of dairy origin termed LHS.

Therefore, the reaction steps of the process according to the present invention comprises:
  inoculating a number of bacterial cells, e.g., *Lactobacillus helveticus* cells, higher than $10^4$, preferably ranging from $10^4$ to $10^{20}$, and more preferably $10^{16}$, into raw *propolis* or a product thereof; the inoculum being obtained by bacterial growth in a suitable culture medium, such as Man Rogosa Shape (MRS) or Brain Heart Infusion (BHI), followed by centrifugation to remove any supernatant;
  adding an aqueous ethanol solution, in which ethanol is present in a percentage by volume lower than 100%, preferably in the range between 5% and 20%, and preferably at about 10%, to give a reaction mixture, typically a suspension; and,
  incubating the reaction mixture at a temperature from 20° C. to 47° C., preferably between 30° C. and 42° C. and more preferably at 37±2° C. for a period of time ranging from 30 minutes to 72 hours, preferably 24 hours, in order to obtain a derivate, typically in a semisolid state.

Advantageously, the aqueous ethanol solution used in the process of the present invention includes one or more dispersant agents, such as polyethylene glycol (PEG), preferably polyethylene glycol 400 (PEG 400) at a concentration preferably lower than 40% v/v, and more preferably 20% v/v.

Qualitative and quantitative composition of a *propolis* derivate obtained by the process of the present invention is preferably determined by the spectroscopic and spectrometric analytical method described herein below; particularly, a UPLC analytical method was used for the quantitative determination of caffeic acid esters, whereas a HPLC analytical method was used to determine the flavonoid content.

Practical carrying out of the enzymatic process of the present invention involved determining the following operating conditions:
1. selection of a suitable bacterial strain;
2. determination of optimal temperature for esterase activity on raw *propolis*;

3. determination of optimal bacterial cells incubation time;
4. determination of optimal percentage of ethanol to be used in the first step;
5. determination of optimal number of bacterial cells/g of *propolis*;
6. synthesis of ester compounds of general formula (1) as reference analytical standard,
7. operating conditions that will be described in detail hereinafter.

According to another aspect of the present invention there is provided a method for purifying raw *propolis* or a semisolid *propolis* derivative obtained as indicated above, comprising the following steps in sequence:

heat dissolution of raw or enzymatically-pretreated *propolis* by a polar organic solvent, preferably ethanol, more preferably being from 60% to 90% ethanol, still more preferably being 90% ethanol, to obtain a dispersion;

cooling of the dispersion thus obtained to room temperature to form a suspension of solid particles in the organic solvent;

filtration of solid particles to separate them from the suspension to obtain a filtrate; subsequently at least one cycle including:

chemical analysis of the filtrate to determine the alcoholimetric volumic titre (or alcoholic degree), the dry residue, and the flavonoids concentration by weight;

dilution of the filtrate with water to adjust the alcoholimetric volumic titre;

cooling of the filtrate to temperatures lower than 0° C. for a time period from 8 to 30 hours thereby obtaining a dispersion;

separation of any insoluble material from the dispersion to isolate a fluid component;

is carried out, after which, the following steps are carried out:

quantitative chemical analysis of the fluid component to determine the weight/volume concentration of flavonoids; and adjustment of the fluid component concentration to obtain a hydroalcoholic derivative with a flavonoid content in the range from 2.5% to 3.0% w/v, preferably 2.6% w/v.

Advantageously, the at least one cycle includes:

dilution of the filtrate with water to bring the alcoholimetric volumic titre to a value in the range from 70% to 80% v/v;

cooling the filtrate to a temperature lower than 0° C. for a time in the range from 8 to 30 hours to obtain a dispersion;

separation of any insoluble material from the dispersion to isolate a fluid component, quantitative chemical analysis of the fluid component to determine the weight/volume concentration of flavonoids;

dilution of the filtrate with water to bring the alcoholimetric volumic titre to a value in the range from 60% to 70% v/v;

cooling of the filtrate to a temperature lower than 0° C. for a time in the range from 8 to 30 hours in order to obtain a dispersion;

separation of any insoluble material from the dispersion to isolate a fluid component, quantitative chemical analysis of the fluid component to determine the weight/volume concentration of flavonoids;

dilution of the filtrate with water to bring the alcoholimetric volumic titre to a value in the range from 50% to 60% v/v;

cooling of the filtrate to a temperature lower than 0° C. for a time in the range from 8 to 30 hours in order to obtain a dispersion; and separation of any insoluble material from the dispersion to isolate a fluid component.

According to another aspect of the present invention there is provided a hydroalcoholic hydrodispersible derivative of *propolis* obtained by the purification method of raw *propolis* or a derivative thereof illustrated above, particularly suitable for use as nutraceutic agent or in cosmetic product formulation.

Further aspects and advantages of the present invention will become better apparent from the following detailed description of some currently preferred embodiments thereof, illustrated hereinbelow as not limiting embodiments of the invention.

EXPERIMENTAL PART 1

Abbreviations

MRS Man Rogosa Sharpe
BHI Brain Heart Infusion
LH5 *Lactobacillus helveticus* 5
PEG Polyethylene Glycol
EtOH Ethanol
EtOAc Ethyl Acetate
THF Tetrahydrofuran
DMAP 4-N,N-Dimethylaminopyridine
DCC N,N'-dicyclohexylcarbodiimide
DCU N,N'-diciclohexylurea
UPLC Ultra Performance Liquid Chromatography
HPLC High Performance Liquid Chromatography Analytical Method For the qualitative and quantitative determination of caffeic acid esters of general formula (1) present in raw *propolis* and/or in a derivative thereof, a UPLC Acquity model (Waters) system was used coupled to a triple quadruple mass spectrometer (MS/MS) equipped with electrospray interface and operating in negative ion mode [ESI(−)]. Analyses were performed under the following experimental conditions. HSS $C_{18}$ chromatographic column (150×2.1 mm, 1.8 μm); column temperature: 60° C.; mobile phase: initially (t=0) 80% eluent A (0.1% formic acid in water) and 20% eluent B (acetonitrile), then from 20% to 35% B in 2 min., then from 35% to 45% B in 2.5 min., then from 35 to 45% B in 10 sec., then 45% B for 40 sec., then from 45 to 95% B in 10 sec., then 95% B for 2 min, and then back to initial conditions in 30 sec.; injection volume: 2 μl; flow rate: 0.6 ml/min.

A Quattromicro (Micromass) model mass spectrometer was used; interface: negative ESI, capillary: 3 kV; cone: 15 eV; collision gas: argon; argon pressure: $2.5 \times 10^{-3}$ mbar; mode: Multiple Reaction Monitoring (MRM); transition pair: 179→135 (for caffeic acid); 247→134 (for 3-methyl-2-butenyl caffeate and 2-methyl-2-butenyl caffeate); 247→135 (for 3-methyl-3-butenyl caffeate); 269→135 (for benzyl caffeate) and 283→135 (for phenylethyl caffeate).

The percentage content of flavonoids in raw *propolis* and/or the derivative thereof was determined using the HPLC- DAD/MS system [HPLC Mod. Alliance 2695 (Waters) interfaced with a diode array detector (DAD) Mod. 2996 (Waters) and Quattromicro (Micromass) model mass spectrometer (MS)].

Analyses were carried out under the following experimental conditions: Symmetry C18 chromatographic column (250×4.6 mm, 5 µm); column temperature: 40° C.; mobile phase: initially 80% eluent A (0.1% formic acid in water) and 20% eluent B (acetonitrile), then from 20% to 35% B in 6 min., then from 35% to 45% B in 40 min., then from 45% to 65% B in 10 min., then from 65% to 95% B in 10 min., then 95% B in 10 min. and back to initial conditions in 3 min.; injection volume: 20 µl; flow rate: 1.5 ml/min.

A Quattromicro (Micromass) model mass spectrometer was used; interface: negative ESI, capillary: 3 kV; cone: 20-40 eV; mode: scanning; acquisition range: 100-800 Da. [C. Gardana et al., *J. Pharm. Biomed. Anal.* 45(3): 390-9 (2007)].

Preliminary Steps

1. Selection of Bacterial Strain.

In a preliminary phase, some food and intestinal bacterial microorganisms were identified and selected in which the presence of enzymes with cinnamoyl-esterase activity is known, for example bacteria listed in the above-reported Table 1. The cinnamoyl esterase activity of these bacteria was evaluated using chlorogenic acid or ethyl ferulate as a substrate, under the following experimental conditions:

Selected bacterial species cells (about $10^{10}$ cells) were suspended in 10 ml of a chlorogenic acid solution (substrate, 0.1 mg/ml) in $H_2O/EtOH$ in which EtoH % by volume was equal to 10%. Reaction mixtures were double incubated at 37° C. and after 24 hours they were centrifuged at 1000×g for 5 minutes. The supernatant was analyzed by the HPLC-DAD analytical method in order to determine the hydrolysis percentage of substrate (chlorogenic acid) to caffeic acid.

The tests results showed that bacteria with the highest enzymatic activity belong to *Lactobacillus* genus. Among the bacteria belonging to *Lactobacillus* genus, different species and strains were selected and experimented on to evaluate whether cinnamoyl esterase activity was species-specific, and then to identify strains having the highest selective enzymatic activity (cinnamoyl esterase), which was determined by using two different substrates, chlorogenic acid and ethyl ferulate, under the following experimental conditions:

bacterial cells (about $10^{10}$) were suspended in 10 ml of a chlorogenic acid or ethyl ferulate solution (substrate, 0.1 mg/ml) in $H_2O/EtOH$ in which EtOH % volume was equal to 10%. The reaction mixtures were double incubated at 37° C. and after 24 hours they were centrifuged at 1000×g for 5 minutes. The supernatant was analyzed using the HPLC-DAD analytical method in order to determine the hydrolysis percentage of substrates to caffeic and ferulic acid, respectively.

This experiment allowed verifying whether the enzymes, present in the tested bacterial strains, had non-selective or selective esterase activity. As a matter of fact, ethyl ferulate and ferulic acid analogue esters are present in raw *propolis*, but they do not have allergenic effects. The results obtained in this experiment are reported in the following Table 2, from which it can be seen that hydrolytic cinnamoyl esterase activity is higher in some *Lactobacillus helveticus* species strains, including strain named LH5.

TABLE 2

Enzymatic activity of strains containing cinnamoyl-esterase enzymes.

| Type | Species | Strain | Activity* ethyl ferulate | Activity* Chlorogenic | % hydrolysis |
|---|---|---|---|---|---|
| Lacto- | helveticus | MIMLH5 | +++ | +++ | 100 |
| bacillus | helveticus | SIM7 | +++ | +++ | 100 |
| | helveticus | CBT17 | ++ | +++ | 92 |
| | helveticus | LH22 | +++ | +++ | 91 |
| | helveticus | LH28 | ++ | ++ | 70 |
| | helveticus | LH23 | ++ | + | <5 |
| | helveticus | LH4 | ++ | ± | <5 |
| | helveticus | LH164 | ++ | − | NT |
| | acidophilus | ATCC4356 | +++ | ++ | 81 |
| | Acidophilus | LA47 | ++ | ++ | 70 |
| | Acidophilus | LA48 | +++ | ++ | 59 |
| | Acidophilus | LA51 | +++ | ++ | 57 |
| | Acidophilus | LA53 | ++ | ++ | 55 |
| | Acidophilus | LA46 | ++ | ± | <5 |
| | Acidophilus | LA50 | ++ | − | NT |
| | fermentum | LB12, LB18 | ++ | ± | <5 |
| | fermentum | LB19 | ++ | + | 42 |
| | casei | LB21, LB22 | + | − | NT |
| | rhamnosus | GG | + | ± | <5 |
| Entero-coccus | faecalis | SMT, TD1, TA15 | + | − | NT |

Legend:
*no activity;
±, poor or uncertain activity;
+, poor;
++, good;
+++, strong.
NT, not tested.

2. Determination of Optimum Temperature for Enzymatic Activity on Raw *Propolis*.

Many reaction mixtures were prepared according to the following procedure, which first provides for the preparation of an inoculum (or cells base) containing a determined number of bacterial cells.

Preparation of Inoculum

A pre-inoculum of *Lactobacillus helveticus* (LH5) was incubated at 37° C. for about 16 hours. 4 ml of the resulting inoculum were incubated in MRS medium (150 ml) at 37° C. for about 16 hours to obtain a broth medium which was submitted to cell count. 4 ml of broth medium were taken as sample and centrifuged for 5 min. at 2000×g to separate cells from broth medium and thus to obtain the desired inoculum.

A *Lactobacillus helveticus* LH5 (about $10^{13}$ cells) cells base obtained according to the procedure described in the paragraph, "Preparation of inoculum" was added to a $H_2O/EtOH$ solution (9:1, 1 ml) containing 1 g of raw *propolis*.

Then, reaction mixtures were double incubated for 24, 48 and 72 hours at the following experimental temperatures: 22, 26, 30, 34, 40, 44 and 47° C. Then the mixtures were cooled, extracted with ethyl acetate (3×20 ml) and centrifuged at 4000×g for 10 min. Solvent of the obtained supernatants was evaporated under nitrogen flow and the residues were suspended in 100 ml of methanol. The solutions thus obtained were first diluted with methanol (1:10) and then analyzed by UPLC-MS/MS.

Figure 1:
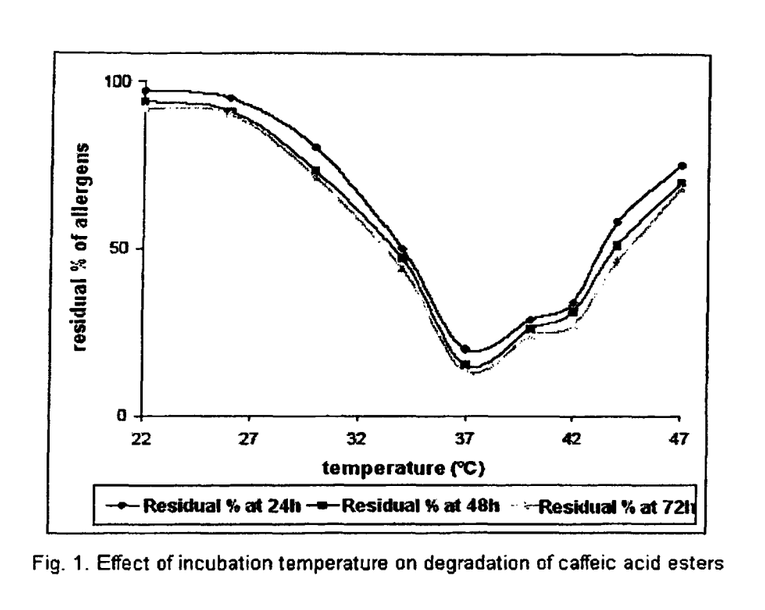
FIG. 1 shows The effect of incubation temperature on degradation of caffeic acid esters.

The obtained results are reported in FIG. 1, which shows that degradation of caffeic acid esters, determined as residual percentage of allergens, that is, esters of general formula (1) also including caffeic acid esters, occurs at a higher rate at a temperature around 37° C.

3. Determination of Optimum Incubation Time for Bacterial Cell Inoculum.

Experiments were carried out according to the following procedure in which the incubation times were in the range from 6 to 72 hours.

Specifically, incubation or reaction times were established at 6, 12, 18, 24, 30, 36, 42, 48, 60 and 72 hours.

Figure 2:
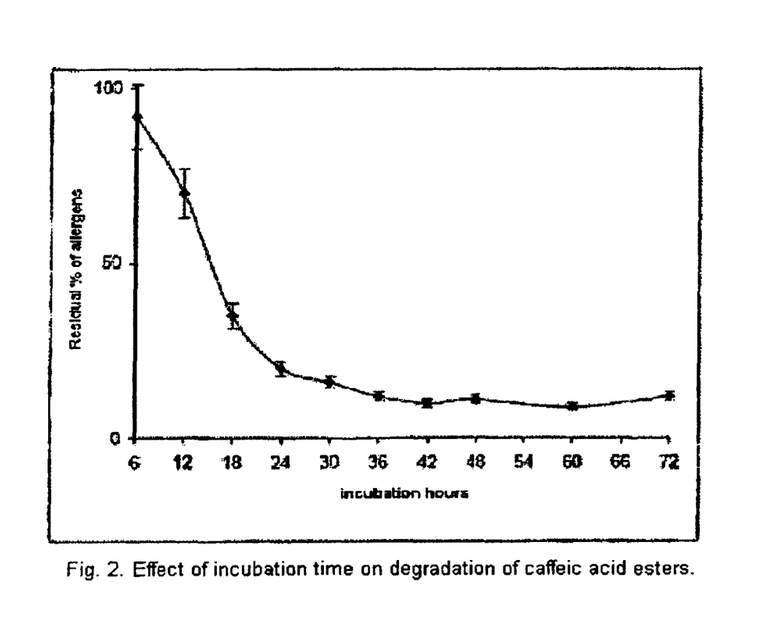
FIG. 2 shows The effect of incubation time on degradation of caffeic acid esters.

A *Lactobacillus helveticus* LH5 inoculum, containing $10^{13}$ cells, prepared according to the above-described procedure in the paragraph "Preparation of inoculum" was mixed with 10.0 ml of a raw *propolis* (10 g) dispersion having a known titre of caffeic acid esters, in a 10% v/v EtOH aqueous solution. The mixture was incubated at 37° C. and the reaction was stopped after a pre-established time (as indicated in the preceding paragraph) by adding ethanol (90.0 ml). The reaction mixture was then extracted with ethyl acetate and the enzymatic activity was evaluated by UPLC-MS/MS analyses of caffeic acid derivates (defined as "allergens" in the graph), whose results are shown in FIG. 2.

The obtained results showed a degradation of caffeic acid esters of about 80% after 24 hours of incubation time. There was no statistically significant increase in degradation for successive times.

Another LH5 inoculum ($10^{13}$ cells) was subsequently prepared according to the above-described experimental procedure, and caused to react with titrated raw *propolis* (10 g) which was previously dispersed in a 10% v/v EtOH aqueous solution (10 ml). Control 1 was prepared with titrated raw *propolis* (10 g) in a 10% v/v EtOH aqueous solution (10 ml) and Control 2 was prepared with an LH5 inoculum ($10^{13}$ cells) in a 10% v/v EtOH aqueous solution (10 ml).

Figure 5:
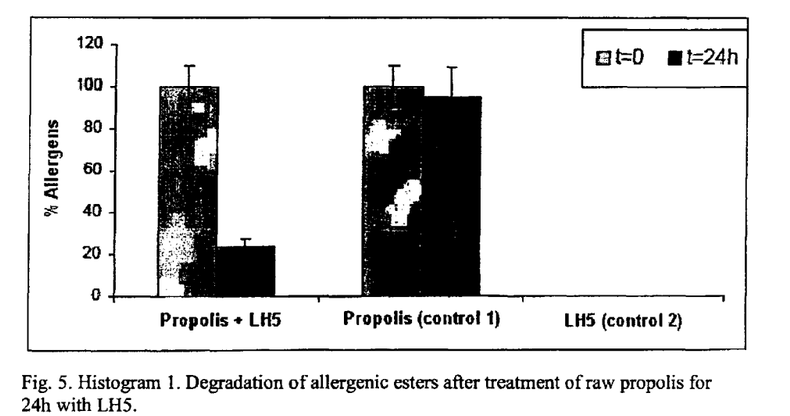
FIG. 5 shows The Histogram 1. Degradation of allergenic esters after treatment of raw *propolis* for 24 h with LH5.

The reaction mixtures were double incubated at 37° C. for 24 hours and then extracted with ethyl acetate (3×30 ml) and the obtained organic mixture was dried under vacuum and the residue suspended with EtOH to be analyzed qualitatively and quantitatively by UPLC-MS/MS and HPLC-DAD, and the results are reported in Histogram 1, as shown in FIG. 5.

4. Determination of Optimal EtOH % (v/v) for Enzymatic Activity.

In order to determine the optimum number of bacterial cells per gram of raw *propolis*, various experiments were carried out according to the following procedure, wherein the number of the used inoculum bacterial cells was varied and selected to be: $10^4$, $10^5$, $10^6$, $10^7$, $10^8$, $10^9$, $10^{10}$, $10^{11}$, $10^{12}$, $10^{13}$, $10^{14}$, $10^{15}$ and $10^{16}$, respectively.

Figure 3:
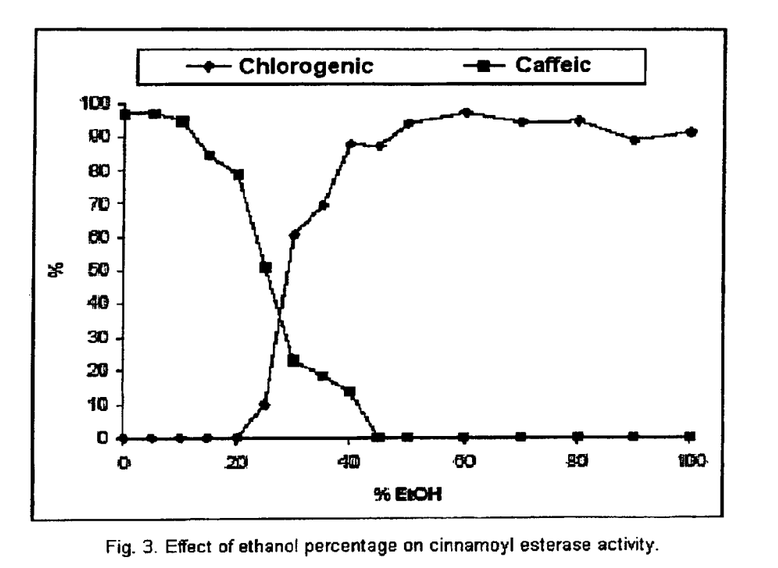
FIG. 3 shows The effect of ethanol percentage on cinnamoyl esterase activity.

The bacterial cells base obtained with the above-described procedure in the paragraph "Preparation of inoculum" was suspended in 10 ml of chlorogenic acid solution (substrate, 1 mg) in $H_2O$/EtOH which was prepared with the percentages of EtOH reported above. The reaction mixtures were double incubated at 37° C. for 22 hours and then centrifuged at 1000×g for 5 minutes. The supernatant was analyzed by HPLC-DAD-MS analytical method in order to determine the hydrolysis percentage of chlorogenic acid to caffeic acid. The results thus obtained are shown in FIG. 3, where EtOH percentage >20% had a detrimental effect on enzymatic activity, whereas an EtOH percentage in the range 5% to 20% makes it possible to obtain an enzymatic hydrolysis of about 80%.

5. Determination of optimal bacterial cells number

In order to determine the optimum number of bacterial cells per gram of raw *propolis*, various experiments were carried out according to the following procedure, wherein the number of the used inoculum bacterial cells was varied and selected to be: $10^4$, $10^5$, $10^6$, $10^7$, $10^8$, $10^9$, $10^{10}$, $10^{11}$, $10^{12}$, $10^{13}$, $10^{14}$, $10^{15}$ e$10^{16}$, respectively.

Figure 4:
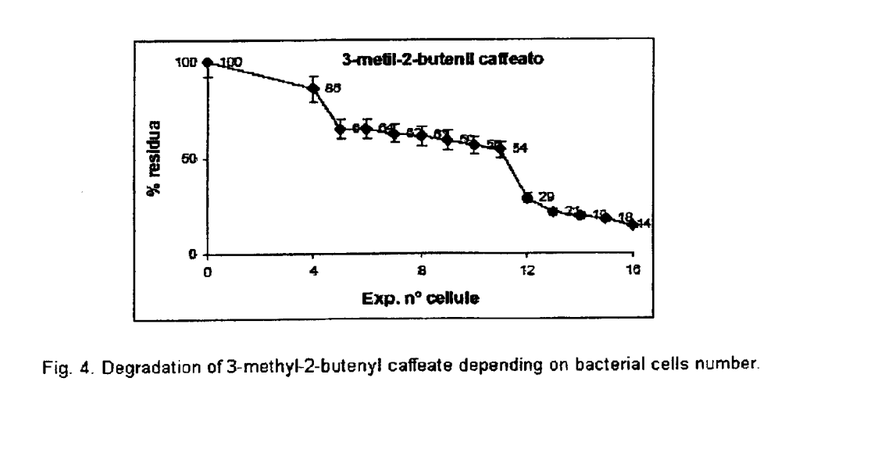
FIG. 4 shows The degradation of 3-methyl-2-butenyl caffeate depending on bacterial cells number.

A *Lactobacillus helveticus* LH5 inoculum obtained as described above under paragraph "Preparation of inoculum", and containing a determined cells number (in the range from $10^4$ to $10^{16}$ as specified in the preceding paragraph), was added to a dispersion of raw *propolis* (1.0 g) in 1.0 ml of a 10% v/v EtOH aqueous solution. The control mixture consisted of *propolis* and a LH5 inoculum containing $10^{13}$ cells in an ethanol aqueous solution (10% v/v, 1 ml). The reaction mixtures were double incubated at 37° C. for 22 hours, then centrifuged at 1000×g for 5 minutes and a *propolis* residue was extracted with EtOAc (3×10 ml). The organic mixture was diluted with EtOH and analyzed through UPLC-MS/MS to determine the content of caffeic acid esters (e.g. 3-methyl-2-buthenyl caffeate) and HPLC-DAD/MS to determine the flavonoid content.

Test results are shown in FIG. 4, where it appears that, under the actual operating conditions, $10^{10}$ cells of LH5/g of raw *propolis* are required to achieve about 50% reduction of 3-methyl-2-butenyl caffeate, which reaches about 80% with $10^{13}$ cells/g of *propolis*.

In Table 3, instead, results of analytical determination (by HPLC-DAD/MS method) of active principle content (e.g. flavonoids) of pre-treated *propolis* samples are shown.

TABLE 3

Amount (%) of polyphenols in raw propolis before and after enzymatic treatment with LH5.

| Component | (%) Before | (%) After | Δ (%) |
| --- | --- | --- | --- |
| Caffei acid | 0.49 | 1.1 | +124 |
| p-Cumaric acid | 1.51 | 1.71 | +13 |
| Ferulic acid | 0.15 | 0.19 | +26 |
| Isoferulic acid | 0.26 | 0.24 | −7 |
| Quercetin derivatives | 22.2 | 21.9 | −1.3 |
| Crisine | 3.07 | 2.96 | −3.5 |
| Pinocembrin | 2.94 | 2.99 | +1.7 |
| Flavonones | 1.7 | 1.72 | +1.1 |
| Pinobanksin acetate | 2.98 | 3.02 | +1.3 |
| Pinobanksin | 0.92 | 0.90 | −2 |
| Pinobanksin-5-ME | 0.44 | 0.48 | +9 |
| Galangin | 2.74 | 2.81 | +2.5 |

6. Synthesis of 3-methyl-2-butenyl Caffeate as Reference Analytical Standard Synthetic Scheme 3-Methyl-2-buten-1-ol (170 μl, 1.67 mmol) was added to a solution of caffeic acid (200 mg, 1.11 mmol) in tetrahydrofuran (THF, 15 ml) and the mixture was stirred at room temperature until complete dissolution. Then 4-N,N-dimethylaminopyridine (DMAP; 13.6 mg, 0.11 mmol) was added, the resulting mixture was cooled to about 4° C. in an ice-water bath and N,N'-dicyclohexylcarbodiimide (DCC, 229 mg, 1.11 mmol) was added. The mixture was stirred at 4° C. for about 10 minutes, then allowed to warm up to room temperature by removal of ice-water bath, and stirred at this temperature for 24 hours. The formed N,N'-diciclohexylurea (DCU) was removed by filtration through a Gooch funnel and the crude reaction solvent was evaporated under reduced pressure (by rotovapor). The residue was taken up with ethyl acetate and filtered again to eliminate any further amount of DCU which was precipitated. In a separation funnel, the organic solution was washed with 0.1N HCl, brine (a NaCl saturated aqueous solution), and finally with a $NaHCO_3$ saturated aqueous solution. The organic phase was dried over anhydrous $Na_2SO_4$ and concentrated to dryness obtaining a crude solid (107 mg), which was then purified by a semi-preparative HPLC, under the conditions described in the next paragraph. A purification step allowed the desired product (90 mg, 0.36 mmol, 33% yield) to be obtained.

Purification of 3-methyl-2-butenyl-caffeate was carried out using a chromatographic system comprising a Mod. Alliance 2695 (Waters) HPLC, a Mod. WFII (Waters) fraction collector and a Mod. 2996 (Waters) diode array detector (DAD). Analyses were carried under the following experimental conditions: C18 Symmetry chromatographic column (250×4.6 mm, 10 µm); column temperature: 40° C.; mobile phase: initially 80% eluent A (0.1% in formic acid in water) and 20% eluent B (acetonitrile), then from 20% to 40% B in 10 min., then from 40% to 90% in 10 sec., then 90% B for 10 min., and then back to the initial conditions in 3 min.; injection volume: 200 µl; flow rate: 3 ml/min.

Example 1

A LH5 inoculum ($10^{13}$ cells/g) prepared according to the experimental procedure described above was caused to react with raw *propolis* (10 g) in a 10% v/v EtOH aqueous solution (10 ml) containing PEG 400 (20% v/v).

Control 1 was prepared with raw *propolis* (10 g) in a 10% v/v EtOH aqueous solution (10 ml), containing PEG 400 (20% v/v), and Control 2 was prepared with a LH5 inoculum ($10^{14}$ cells) in a 10% v/v EtOH aqueous solution (10 ml) containing PEG 400 (20% v/v).

The reaction mixtures were double incubated at 37° C. for 24 hours then centrifuged at 1000×r for 5 minutes to obtain a semisolid residue. A portion of the residue (1 g) was taken and extracted with ethyl acetate (3×30 ml) and the organic mixture was diluted with EtOH for UPLC-MS/MS and HPLC-DAD quantitative and qualitative analyses.

Example 2

Two LH5 inoculums ($10^{12}$ and $10^{13}$ cell/g, respectively), prepared according to the above described procedure, were caused to react with raw *propolis* (1 Kg) in a 10% v/v EtOH aqueous solution (2 l) containing PEG 400 (20% v/v).

The reaction mixtures were double incubated at 37° C. for 96 hours, and 10 g portions were taken every 24 hours. The various portions were then centrifuged at 1000×g for 5 minutes to obtain a semisolid residue from each one. A portion of the semisolid residue (1 g) was extracted with ethyl acetate (3×30 ml). The obtained organic mixture was diluted with EtOH for UPLC-MS/MS for the HPLC-DAD quantitative and qualitative analyses.

Raw *propolis* or one pre-treated according to the enzymatic process of the present invention providing a *propolis* derivative, typically in a semisolid state, is purified or impoverished of some components thereof according to a method that makes it possible to prepare a hydroalcoholic hydrodispersible derivative of *propolis* to be used typically as such or in formulations of nutraceutics and cosmetic products.

This purification method, also the subject-matter of the present invention, comprises the following sequential steps:

heat dissolution with a polar organic solvent, preferably ethanol, and preferably 90% ethanol, to obtain a solution (the term "heat", means "at a temperature higher than 20° C. and lower than 60° C.");

cooling of the solution to room temperature to form a suspension;

separation, typically by filtration, of the solid particles in suspension to obtain a filtrate;

chemical analysis of the filtrate to determine the alcoholimetric volumic titre (or alcoholic degree), dry residue, and flavonoids concentration by weight/volume;

dilution of the filtrate with water in order to bring the alcoholimetric volumic titre (or alcoholic degree) to a value in the range 70% to 80%, expressed in volume/volume percentage of ethanol;

cooling of the filtrate to a temperature lower than 0° C., preferably between 0° C. and −20° C. for a period of time from 8 to 30 hours;

separation of the insoluble materials, such as wax and fatty substances, from the filtrate, e. g. by centrifugation, filtration or decantation, to isolate a fluid component;

quantitative and qualitative chemical analysis of the fluid component to determine the flavonoids concentration expressed by weight/volume;

dilution of the filtrate with water to bring the alcoholimetric volumic titre (or alcoholic degree) to a value in the range from 60 to 70%, expressed in volume/volume percentage of ethanol;

cooling the filtrate to temperatures lower than 0° C., preferably between 0° C. and −20° C. for a time in the range between 8 and 30 hours;

separation of the filtrate, e. g. by centrifugation, filtration or decantation, of insoluble material, e. g. waxes or fat, in order to isolate the fluid component;

quantitative chemical analysis of the fluid component in order to determine the weight/volume concentration of flavonoids;

dilution of the filtrate with water to bring the alcoholimetric volumic titre (or alcoholic degree) to a value in the range from 50 to 60%, expressed in volume/volume percentage of ethanol;

cooling the solution to temperature lower than 0° C., preferably between 0° C. and −20° C. for a time in the range between 8 and 30 hours in order to obtain a dispersion;

separation of the filtrate, e. g. by centrifugation, filtration or decantation, of insoluble material, such as fat, to isolate the fluid component;

quantitative chemical analysis of the fluid component to determine the weight/volume concentration of flavonoids;

adjustment of the fluid component concentration to obtain a hydroalcoholic hydrodispersible derivative with a flavonoids content ranging from 2.5% to 3.0% w/v, preferably 2.6% w/v.

Such an adjustment of the fluid part concentration can be carried out by dilution with water or by partial removal of solvent, typically by distillation, to reach a desired flavonoids titre or content.

For analytical determinations of alcoholimetric volumic titre or alcoholic degree, dry residue and flavonoids concentration, determinations performed on the fluid component as an intermediate product of the process of the present invention, the following analytical methods are used: alcoholmeter method, weighing method by using a thermo-balance, and HPLC-DAD method, respectively.

EXPERIMENTAL PART 2

Analytical Methods

1. Determination of Alcoholimetric Volumic Titre or Alcoholic Degree.

The alcoholimetric volumic titre (avt) was determined via an automatic Super DEE SV distiller and the electronic hydrostatic Densimat balance. Data processing software was Gibertini Alcosoft 2.

Equipment was in accordance with official methods described in EEC Regulation n. 2676/90 from the commission of Sep. 17, 1990, which determines UE community analytical methods to be used in the wine field.

The sample to be analyzed (100 ml) is first placed in a distillation ampoule, followed by addition of suitable reagents (a water, anti-foam solution, sodium chloride and potassium alum mixture) and then distillation was started. During distillation, the distillate was collected in a calibrated flask and placed on the precision balance arm that stops the distillation when a pre-established amount of distillate is obtained. Finally, the % v/v alcoholimetric volumic titre (ethyl alcohol ml in a solution of 100 ml) was derived from the distillate relative density (suitably brought to 100 ml exact volume) at 20° C.

2. Determination of Dry Residue

Dry residue was determined by the official method reported in the European Pharmacopeia $6^{th}$ Ed., chapter 2.2.32 "Loss on drying" by using MB 35 moisture analyzer (Ohaus Corporation).

The method provides for the sample to be analyzed being placed onto the balance plate, which is suitably set to zero. Measurement of the sample dry residue is carried out at 105° C. when, after complete evaporation of solvent, the sample reaches a constant weight. Data are expressed as % w/w.

3. Determination of Flavonoid Content

Flavonoids content (concentration expressed as g/100 ml or w/v %) was established by using the HPLC-DAD system [HPLC system interfaced with a diode array detector (DAD)] under the following experimental conditions: Symmetry C18 chromatographic column 3.5 µm, 150×2.1 mm (Waters); column temperature: 30° C.; samples temperature: 20° C.; mobile phase: A: trifluoroacetic acid (TFA) 0.1%; B: 0.1% TFA in acetonitrile; gradient 15-25% B for 10 min., 25%-40% B in 30 min., 40%-55% B in 15 min., 55%-70% B in 20 min., 70%-90% B in 2 min. and 90% B for 3 min.; flow rate: 0.25 ml/min.; acquisition: 200-450 nm: processing wave length: 290 nm.

Further aspects of the various steps of the purification method herein illustrated will become better apparent in the detailed description of the currently preferred, but non-limiting, embodiment of the present invention.

Example 3

Propolis derivative in a semisolid state (100 kg) was dissolved with 90% ethanol (282 l; derivative:ethanol ratio=about 1:3 w/v) by stirring the mixture at 38° C. for about 15 hours. The solution was cooled by lowering the temperature to 20° C. in about 7 hours, thus obtaining a suspension which was then filtered, and the filtrate was collected, weighed (320 l) and analyzed for determining its alcoholic degree, dry residue and flavonoids content. From the analysis it was found that the filtrate had a 76.8° alcoholic degree, a 19.4% dry residue and a 6.5% w/v flavonoids concentration. The filtrate was diluted with water (84 l) until reaching an alcoholic degree of 55-60% then it was cooled to −15° C. in about 15 hours and finally centrifuged for about 7 minutes at 4° C. for removing any insoluble material and obtaining a supernatant (31 l). The supernatant was analyzed by HPLC-DAD. The analysis showed that the content in flavonoids was 3% w/v, which was brought down to 2.6% by dilution with 96% thanol (48 l) to obtain a *propolis* hydroalcoholic derivative (363 l) having a 60±1.5% alcoholic degree.

The method taught by JP-7-8185 has a number of drawbacks in comparison with the method according to the application invention, which are hereinbelow summarized.

First of all, the used enzymes, above all oxidoreductase, are not specific, and thus cause a remarkable decrease in the amount of active principles of *propolis*, i. e. the flavonoids. Oxidoreductases have been mentioned above, whereas carboxylesterases are less invasive than oxidoreductases, although they hydrolyze the esters of flavonoids (e.g. pinobanksin acetate) and other phenols (e.g. p-cumarate) traceable in *propolis*. Carboxylesterases therefore change the characteristic finger-printing of the *propolis* extract.

The process according to the application invention, instead, provides the use of probiotics having enzymatic activities, i.e. cinnamoyl-esterase, which are specific for the allergenic compounds of *propolis*. In the process of the application invention the flavonoid content is not changed and the *propolis* extract is maintained as natural as possible.

Hereinafter, the reaction mechanism of the process of the present invention is compared with the reaction mechanism of a method according to JP-7-8185, i. e. a method using carboxylesterase.

flavonoid contained in propolis probiot → none hydrolitic reaction

As will be understood, industrially obtained enzymes are quite expensive to buy, and thus the method proposed by JP-7-8185 is expensive and difficult to be carried out on an industrial scale. On the contrary, the process of the application invention, is carried out by using probiotics, i.e. microorganisms which can be produced at low costs and in large amounts, and thus such process can be advantageously adopted in industry.

Moreover, the oxido-reductase causes the formation of polymers, which will be included in the hydroalcoholic extract of *propolis*.

At the end of the method JP-7-8185, it is evaluated the quantitative decrease of the allergens in the *propolis*. No analyses have been suggested in order to evaluate the content of active principles after the enzymatic treatment. On the contrary, at the end of the process according to the application invention, specific and quantitative evaluations both in so far as the allergenic substances and the active principles are performed.

In addition, according to JP-7-8185 (see for example, paragraph [0030], Example 3), a high amount of ethanol for the extraction step is required, the alcohol degree must then be decreased with water, the solvent is eliminated after the enzymatic reaction, and finally dispersion in ethanol occurs. Clearly such procedure cannot be carried out on an industrial scale, owing to the high cost of ethanol. On the contrary, the present application provides for a substantial reduction of allergenic substances in water ambient and a subsequent extraction with solvent in such a way as to avoid undesired waste of ethanol and to make it possible to apply the process of extraction in industry.

According to the method of JP-7-8185, standardized *propolis* cannot be obtained, this being an essential requirement for erboristic and pharmaceutical industry. On the contrary, according to the present application it is possible to reduce the allergenic substances and standardize the hydro-alcoholic extract and the hydrodispersibility thereof.

In so far as the extraction process is concerned, the method of the present application aims at obtaining hydroalcoholic *propolis* extracts which are hydrodispersible and standardized both in the content of flavonoids and derivatives of cinnamic acid (phenolic acid). Such extracts can be used as such for producing dried *propolis* extracts usable for obtaining solid preparations (e. g. tables, ointments, candies), or syrups, mouthwashes or the like preparations.

More particularly, the extraction and purification method of the present invention provides a titred extract including flavonoids at a concentration of 2.5+0.1% and phenolic acids at a concentration of 0.5+0.1%. Moreover, the purification method allows the drastic reduction of the content of fat components (fat acids, short-chain triglycerides and waxes), which are to be found in raw *propolis*. The hydroalcoholic extract of *propolis*, obtained with the method of the application invention, includes less than 0.5% of fat component.

The amount of fats is gravimetrically determined after a reflux with chloroform-methanol (1:3, v/v) in a Soxhlet's extractor. The reduced amount of "fat matter" renders the hydroalcoholic abstract of *propolis* dispersible in water without any risk that micelles and frustules are produced as a consequence of the precipitation of insoluble material.

The hydrodispersibility of *propolis* extract obtained with the method of the present invention has low content of fat matter. Thus, the active components, polyphenols, are better absorbed at an enteric level after oral administration. The fat part, in fact, would act as a passive barrier for the absorption of nutrients and phytocompounds, thus affecting the systemic activity thereof.

Accordingly, the inventors of the present application provide a fractioned purification method which allows the substantial reduction of the content of fats, thus keeping the active part of *propolis* unaltered. The standardization and hydrodispersibility makes the hydroalcoholic extract of *propolis* of the present invention a unique product in the phytotherapic and pharmacological field.

Moreover, the above-mentioned features distinguish the method of the present invention with respect to any prior art method.

In so far as EP-0 019 993 is concerned, since the used percentage of ethanol is too low, it is impossible to extract either the fat part of *propolis*, or the active part thereof, the flavonoids. Laboratory tests have shown that flavonoids in *propolis* are quantitatively extracted with an ethanol solution at least 60% or more (v/v) and at a temperature in the range of 35 to 45° C.

It should also be noted that in such prior art document no evidence is given as to the extraction of fats and flavonoids, whereas the product obtained according to the method of the present invention includes an amount of active principles which is standardized and the content of fats is lower than 0.5%.

According to the present invention, during a first step the allergenic substances of raw *propolis* are drastically reduced by a microorganism, and the pretreated *propolis* is subsequently extracted and purified in order to obtain hydroalcoholic hydrodispersible *propolis* extracts having a known titre.

The raw *propolis* is initially titred in order to determine the amount of active compounds and allergens. The raw *propolis* is then pretreated with a microorganism having cinnamoylesterase activity, which hydrolyzes the allergens only. The pretreated *propolis* is then extracted with ethanol at a controlled temperature and after a predetermined time interval the solid residue is removed and the content of active-compounds, allergens, alcoholic degree and dried residue of liquid thus-obtained is evaluated.

On the basis of the results thus obtained, a fractioned purification is carried out by adding water and short cooling of the dispersion. The fractioned purification with water is not referred to, nor taught in the prior art documents referred to above. In the method of the present invention, the fat components are gradually eliminated without altering or varying the amount of active principles. The method can be adapted to any *propolis* having a different ethnogeographic origin, which means *propolis* having different content of active principles and allergens. Moreover, according to the method of the present invention, no ethanol is wasted, and an increased amount of hydroalcoholic extract is obtained.

These advantages, together with the standardization of the product, render the method of the present invention industrially applicable and economically advantageous.

The enzymatic process of the present invention for pre-treating *propolis*, the method of purification of *propolis* or a derivative thereof, as well as the derivatives obtained through such process and method are susceptible to numerous variations within the scope as defined by the tenor of the following claims.

The invention claimed is:

1. A process for pre-treating *propolis* comprising at least one allergenic substance of general formula (1)

(1)

wherein R is an alkyl or alkenyl selected from the group comprising 3-methyl-2-butenyl, 2-methyl-2-butenyl, 3-methyl-3-butenyl, benzyl and phenylethyl,
wherein
raw *propolis* is caused to react at a temperature of 37° C.±2° C. with a microorganism comprising at least one enzyme having cinnamoyl-esterase activity to obtain a semisolid *propolis* derivative with a reduced content of allergenic substances.

2. The process according to claim 1, wherein said at least one enzyme with selective esterase activity is of bacterial origin.

3. The process according to claim 2, wherein said at least one enzyme with selective esterase activity is produced by at least one bacteria from a genus selected from the group consisting of *Lactobacillus, Carnobacterium, Enterococcus, Streptococcus* and *Bifidobacterium*.

4. The process according to claim 3, wherein said at least one enzyme with selective esterase activity is produced by at least one bacterial strain of the species selected from the group consisting of *Lactobacillus paracasei, Lactobacillus acidophilus, Lactobacillus helveticus, Lactobacillus casei, Lactobacillus fermentum, Lactobacillus rhamnosus, Carnobacterium maltaromaticum, Carnobacterium divergens, Enterococcus faecalis, Enterococcus faecium, Streptococcus thermophilus, Bifidobacterium bifidum, Bifidobacterium pseudocatenulatum, Bifidobacterium longum, Bifidobacterium animalis* and *Bifidobacterium adolescentis*.

5. The process according to claim 3, wherein at least one enzyme with selective esterase activity is produced by at least one bacterial strain of *Lactobacillus helveticus*.

6. The process according to claim 2, wherein said reaction step comprises:
   inoculation of a number of bacterial cells in a range from $10^4$ to $10^{20}$;
   addition of an ethanol aqueous solution, wherein ethanol content ranges from about 5% to about 20% by volume, thereby obtaining a reaction mixture; and,
   incubation of said reaction mixture for a time period from 30 minutes to 72 hours, thereby obtaining a derivative, typically semisolid derivative.

7. The process according to claim 6, wherein said ethanol aqueous solution contains at least one dispersant agent.

8. The process according to claim 6, wherein said ethanol aqueous solution contains at least one dispersant agent, and wherein said at least one dispersant agent comprises polyethylene glycol.

9. The process according to claim 6, wherein said incubation period is about 24 hours.

10. The process according to claim 6, wherein the number of bacterial cells is $10^{16}$.

11. The process according to claim 6, wherein the ethanol content is 10% by volume.

12. The process according to claim 8, wherein the at least one dispersant agent comprises polyethylene glycol 400.

13. A process for pre-treating *propolis* comprising at least one allergenic substance of general formula (1)

(1)

wherein R is an alkyl or alkenyl selected from the group comprising 3-methyl-2-butenyl, 2-methyl-2-butenyl, 3-methyl-3-butenyl, benzyl and phenylethyl,
wherein
raw *propolis* is caused to react with a microorganism comprising at least one enzyme having cinnamoyl-esterase activity to obtain a semisolid *propolis* derivative with a reduced content of allergenic substances, and
an ethanol aqueous solution is added to the raw *propolis* and the microorganism wherein the ethanol content ranges from 5% to 20% by volume, thereby obtaining a reaction mixture.

* * * * *